United States Patent
Todd et al.

(10) Patent No.: US 8,672,908 B2
(45) Date of Patent: Mar. 18, 2014

(54) CONVEX BARRIER RING

(75) Inventors: Russell J. Todd, Ingleside, IL (US); Brock E. Masters, Toronto (CA)

(73) Assignee: Hollister Incorporated, Libertyville, IL (US)

(*) Notice: Subject to any disclaimer, the term of this patent is extended or adjusted under 35 U.S.C. 154(b) by 0 days.

(21) Appl. No.: 13/402,558

(22) Filed: Feb. 22, 2012

(65) Prior Publication Data

US 2012/0232506 A1    Sep. 13, 2012

Related U.S. Application Data (60) Provisional application No. 61/449,937, filed on Mar. 7, 2011.

(51) Int. Cl.
*A61F 5/448* (2006.01)

(52) U.S. Cl.
USPC ........... 604/344; 604/317; 604/327; 604/332; 604/338; 604/339

(58) Field of Classification Search
None
See application file for complete search history.

(56) References Cited

U.S. PATENT DOCUMENTS

| | | | |
|---|---|---|---|
| 3,076,458 A | 2/1963 | Mason | |
| 3,557,790 A | 1/1971 | Hauser | |
| 4,109,657 A | 8/1978 | Carrington | |
| 5,492,943 A | 2/1996 | Stempel | |
| 5,811,116 A * | 9/1998 | Gilman et al. | 424/443 |
| 5,834,009 A * | 11/1998 | Sawers et al. | 424/443 |
| 6,033,390 A | 3/2000 | von Dyck et al. | |
| 6,135,986 A | 10/2000 | Leisner | |
| 6,350,255 B1 | 2/2002 | von Dyck et al. | |
| 6,350,256 B1 * | 2/2002 | Palumbo et al. | 604/339 |
| 6,464,674 B1 | 10/2002 | Palumbo et al. | |
| 6,485,476 B1 | 11/2002 | von Dyck et al. | |
| 6,491,673 B1 | 12/2002 | Palumbo et al. | |
| 6,508,794 B1 | 1/2003 | Palumbo et al. | |
| 6,551,292 B1 | 4/2003 | D'Acchioli et al. | |
| 6,569,134 B1 * | 5/2003 | Leise et al. | 604/332 |
| 6,673,056 B2 | 1/2004 | Metz et al. | |
| 6,740,067 B2 | 5/2004 | Leise, Jr. et al. | |

(Continued)

FOREIGN PATENT DOCUMENTS

| | | |
|---|---|---|
| DE | 20307688 U1 | 7/2003 |
| EP | 1275357 A2 | 10/1997 |

(Continued)

OTHER PUBLICATIONS

Advertisement for Ileostomy, Colostomy, Ileal Bladder, and Ureterostomy Custom-Fabricated Appliances, Faceplates and Pouches by the Perma-Type Company, Inc. of Plainville, CT published in Ostomy Quarterly, vol. 35, No. 2, Winter 1998.

(Continued)

*Primary Examiner* — Jackie Ho
*Assistant Examiner* — Eric Bryant
(74) *Attorney, Agent, or Firm* — Levenfeld Pearlstein, LLC (57) ABSTRACT

A convex barrier ring, that includes a generally oval shaped body and tapered peripheral end portions, is provided. In use, the convex barrier ring is sealed against peristomal skin surfaces such that the tapered peripheral end portions are aligned with folds or creases in the skin surfaces to reduce leakage of stomal effluent. The convex barrier can also have an oval stoma-receiving aperture to provide an improved fit for oval or loop stomas.

18 Claims, 5 Drawing Sheets

(56) References Cited

U.S. PATENT DOCUMENTS

| | | |
|---|---|---|
| 6,796,974 B2 | 9/2004 | Palumbo et al. |
| 6,916,312 B2 | 7/2005 | Kondo et al. |
| 6,926,701 B2 | 8/2005 | Burns et al. |
| 7,087,041 B2 | 8/2006 | von Dyck et al. |
| 7,101,357 B2 | 9/2006 | Tanaka et al. |
| 7,341,578 B2 | 3/2008 | Bulow |
| 7,422,578 B2 | 9/2008 | Shan |
| 7,586,019 B2 | 9/2009 | Oelund et al. |
| 7,927,320 B2 | 4/2011 | Goldwasser et al. |
| 7,931,631 B2 | 4/2011 | Pedersen et al. |
| 2003/0171737 A1* | 9/2003 | Leise et al. .................. 604/540 |
| 2004/0087920 A1 | 5/2004 | Etheredge |
| 2004/0106908 A1 | 6/2004 | Leise et al. |
| 2005/0177119 A1 | 8/2005 | Tsai |
| 2007/0191794 A1 | 8/2007 | Cline et al. |
| 2007/0255240 A1 | 11/2007 | Clok |
| 2008/0154220 A1 | 6/2008 | Gaffney |
| 2008/0319368 A1 | 12/2008 | Lykke et al. |
| 2009/0043271 A1 | 2/2009 | Winther |
| 2009/0227972 A1 | 9/2009 | Aragones |
| 2009/0234312 A1 | 9/2009 | O'Toole et al. |
| 2009/0311307 A1 | 12/2009 | Lykke |
| 2010/0022933 A1 | 1/2010 | Oelund et al. |
| 2010/0324511 A1* | 12/2010 | Dove et al. ................ 604/342 |

FOREIGN PATENT DOCUMENTS

| | | | |
|---|---|---|---|
| EP | 1894547 A1 | 3/2008 | |
| EP | 1413268 B1 | 4/2009 | |
| GB | 2023007 A | 12/1979 | |
| JP | 07289574 A | 7/1995 | |
| JP | 2005519674 A | 7/2005 | |
| JP | 2010184144 A | 8/2010 | |
| WO | 03075808 A1 | 9/2003 | |
| WO | 2010054662 A2 | 5/2010 | |
| WO | WO 2010/054662 * | 5/2010 | ............. A61F 5/445 |
| WO | 2011050816 A1 | 5/2011 | |
| WO | 2012079592 A1 | 6/2012 | |

OTHER PUBLICATIONS

Advertisement for Nu-Comfort Skin Barrier Pouches by Nu-Hope Laboratories; Inc. of Pacoima, CA published in Ostomy Quarterly, vol. 35, No. 1, Fall 1997.

* cited by examiner

CONVEX BARRIER RING

CROSS-REFERENCE TO RELATED APPLICATION DATA

This application claims the benefit of priority of Provisional U.S. Patent Application Ser. No. 61/449,937, filed Mar. 7, 2011 entitled, "CONVEX BARRIER RING."

BACKGROUND

The present disclosure relates to a skin barrier for ostomy appliances, and more particularly to an oval shaped convex barrier ring.

Barrier rings are used with ostomy appliances to aid in sealing such appliances against peristomal skin surfaces and thereby protect those surfaces from exposure to stomal effluent as well as to prevent leakage of the effluent from about stoma-receiving openings of the pouches. However, the topography of stomas and peristomal surfaces surrounding stomas vary among patients, and sealing the ostomy appliances against such different peristomal surfaces and stomas remain as an area for further improvements.

For example, a stoma may protrude more or less, or may even be flush or recessed. Ostomy patients with flush or recessed stomas have found that if external pressure is applied in the peristomal region, sufficient protrusion of the stoma may occur to aid in the discharge of effluent directly into the collection pouch, thereby prolonging the effectiveness of the adhesive seal between the faceplate and the peristomal skin surface. Skin irritation and patient discomfort may also be greatly reduced. Thus, convex inserts and convex pressure rings, such as ADAPT® convex barrier rings available through the assignee of the present application, have been developed to apply pressure around such peristomal region.

Because of the inherent severe medical, social, economical and personal concerns related to the need for use of an ostomy appliance, improvements in barrier rings to provide better sealing function and/or comfort is an important factor in the quality of life of wearers and therefore in the consequent health and psychological aspects of the wearer. Any appreciable improvement of such ostomy appliances is therefore of great importance to the increasing number of such wearers. The present disclosure provides improved convex barrier rings according to various embodiments to enhance comfort and sealing between the peristomal skin surfaces and the ostomy appliances.

BRIEF SUMMARY

Barrier rings according to various embodiments have a convex surface contour and a generally oval peripheral shape to provide improved sealing of ostomy appliances against peristomal surfaces. Further, the barrier rings can have an oval shaped stoma-receiving aperture to apply even pressure on the peristomal surfaces surrounding non-round stomas such as oval and loop stomas. Preferably, the convex oval barrier rings have tapered peripheral end portions, which can aid in sealing the ostomy appliances against folded or creased skin surfaces.

In one aspect, a barrier ring for attaching an ostomy appliance to a peristomal skin surrounding a stoma is provided. The barrier ring includes a generally oval shaped body with tapered peripheral end portions, a convex proximal bodyside surface, a flat bottom surface, and a stoma-receiving aperture.

In another aspect, a convex barrier ring for attaching an ostomy appliance to peristomal skin surrounding a stoma includes a convex proximal bodyside surface, a flat bottom surface, an oval stoma-receiving aperture, and a cat-eye shaped body having elongated peripheral end portions. The elongated peripheral end portions may include ridges.

In yet another aspect, a barrier ring for attaching an ostomy appliance to a peristomal skin surrounding a stoma is provided. The barrier ring includes a generally oval shaped body with tapered peripheral end portions defining a major axis and a minor axis, a bodyside surface, a bottom surface, and a stoma-receiving aperture. The bodyside surface, when viewed in a cross-section taken along the major axis defines a convex surface transitioning to a concave surface from the stoma-receiving aperture to a respective tapered peripheral end portion.

In another aspect, a method of attaching an ostomy appliance to peristomal folded or creased skin surfaces surrounding a stoma of a wearer is provided. The method includes providing a convex barrier ring that includes a convex proximal bodyside surface, a flat bottom surface, an oval stoma-receiving aperture, and a cat-eye shaped body having elongated peripheral end portions, wherein the elongated peripheral end portions include ridges. Further, the method includes placing the flat bottom surface on an adhesive side of a faceplate of the ostomy appliance, arranging the ostomy appliance assembled with the convex barrier ring around the stoma such that the stoma is arranged in the oval stoma-receiving aperture, and sealing the convex proximal bodyside surface against the peristomal skin surfaces such that the elongated peripheral end portions are aligned with the skin folds or creases.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein.

DETAILED DESCRIPTION

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

A barrier ring is used to fill in or caulk uneven skin contours near a stoma and to improve seal against the stoma. However, skin folds and creases formed from various postures, for example, sitting or bending, or from obesity, often reduce or break the seal around such areas and cause undesirable leakage. Similar seal problems also exist with patients with oval shape stomas, loop stomas, or other non-round stomas. For example, when patients with a loop stoma and/or skin folds due to obesity use a conventional round convex ring, leakage has been frequently observed around the 6 and 12 o'clock positions of the barrier ring due to reduced pressure against skin in those areas.

To overcome this problem, convex barrier rings having a generally oval shape body with tapered peripheral end portions are provided according to various embodiments. In FIGS. 1-7, a convex barrier ring 10 including an oval or elliptical stoma-receiving aperture 12 and a generally oval shaped body 11 with tapered peripheral end portions 14, 16 is illustrated according to an embodiment. The tapered, oval shaped body 11 that tapers at either side to terminate in the tapered peripheral end portions 14, 16 having a relatively small radius of curvature, such that the body 11 in plan view resembles a cat-eye (see e.g. FIGS. 2 and 3), thus the barrier rings having such a shape are also referred to herein as cat-eye barrier rings. The oval shaped stoma-receiving aperture 12 can improve the stoma fit, particularly for non-round stomas such as loop stomas and oval stomas. Further, the convexity of the body 11 and the elongated tapered peripheral end portions 14, 16 provide improved adhesion against uneven or folded or creased skin surfaces.

Figure 1:
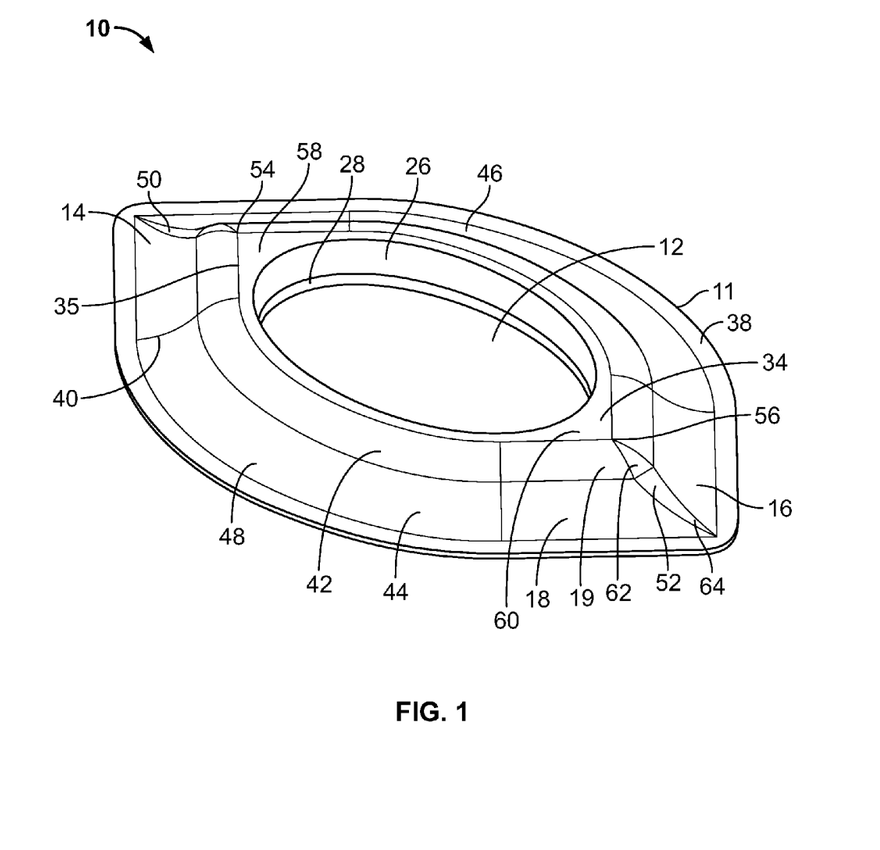
FIG. 1 is a perspective view of a convex barrier ring having a tapered oval shape according to an embodiment.
Figure 2:
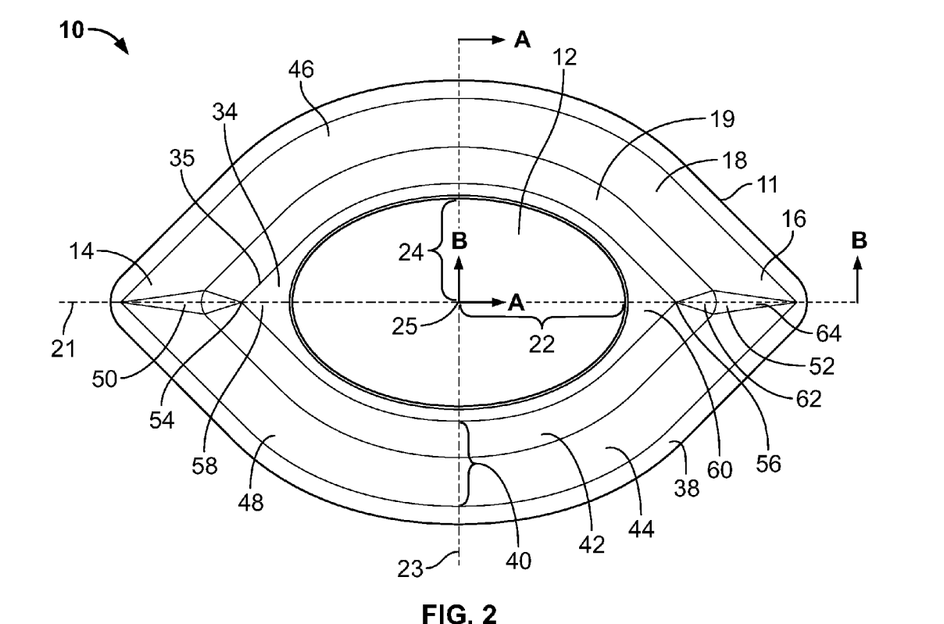
FIG. 2 is a top view of the convex barrier ring of FIG. 1.
Figure 3:
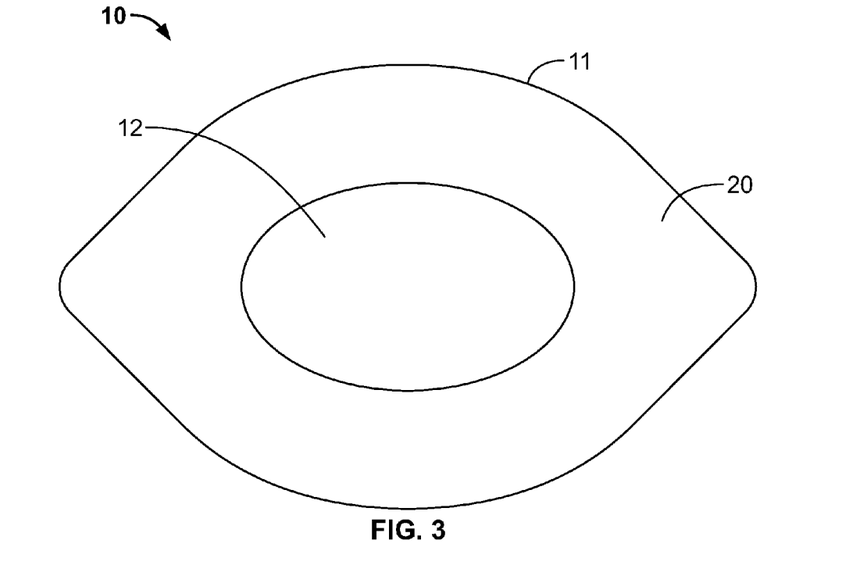
FIG. 3 is a bottom view of the convex barrier ring of FIG. 1.
Figure 4:
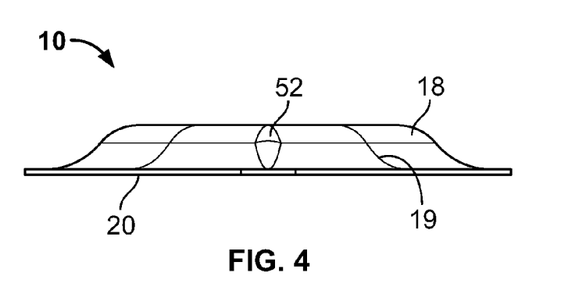
FIG. 4 is a front view of the convex barrier ring of FIG. 1.
Figure 5:
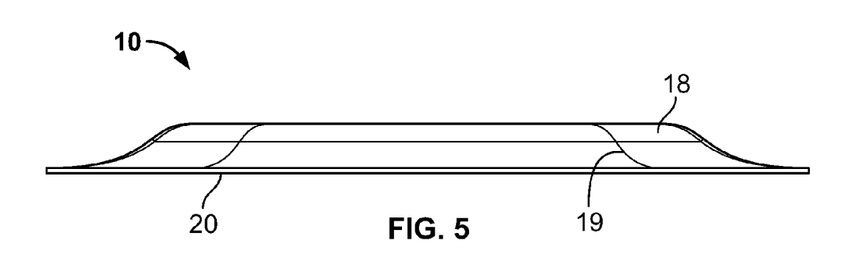
FIG. 5 is a side view of the convex barrier ring of FIG. 1.

The barrier ring 10 has a top surface 18 having a convex contour 19 (FIGS. 1, 2, 4 and 5) and a flat bottom surface 20 (FIGS. 3, 4 and 5). In use, the flat bottom surface 20 of the barrier ring 10 is first applied on the adhesive side of an ostomy pouch faceplate (not shown), then the ostomy pouch, assembled with the barrier ring 10, is applied about the stoma in a usual manner such that the tapered peripheral end portions 14, 16 are positioned generally horizontally to fit in the folded or creased skin. Because the top surface 18 is the surface that contacts the skin, the top surface 18 is also referred to herein as a proximal bodyside surface.

The barrier ring 10 is formed of a suitable skin barrier material. The skin barrier material referred to herein may be any of the many skin barrier materials known in the art which is suitable for molding to form the barrier rings according to various embodiments. Preferably, the barrier ring 10 is formed of a flexible medical grade adhesive material, such that the barrier ring 10 can be stretched, cut and/or stacked together to improve the fit of the ostomy pouch system. For example, the barrier ring 10 can be formed of a pressure sensitive adhesive composition, such as that disclosed in U.S. Pat. No. 5,492,943 assigned to the assignee of the present application, which is incorporated herein in its entirety by reference. The barrier ring 10 formed of such flexible materials can apply soft pressure around the stoma to improve comfort, and reduce pressure sores, hernias, and other skin conditions, such as peristomal pyoderma gangrenosum, which can result from using firm convex barrier rings. Further, the flexibility of the material allows the user to stretch or manipulate the shape of the barrier ring 10 to better fit the stoma and peristomal skin surfaces.

The barrier ring 10 can be provided with protective coverings (not shown) on both top and bottom sides, which are removed by the user before using. The protective coverings can be formed of any suitable materials, such as paper or a polymeric film, and preferably coated with a release coating such as silicone.

Referring again to FIGS. 1-7, the illustrated convex barrier ring 10 has a generally oval shaped stoma-receiving aperture 12. The stoma-receiving aperture 12 is defined by an upper annular wall 26 and a lower annular wall 28. As shown in partial cross-sectional views of the barrier ring 10 (FIGS. 6 and 7), the upper annular wall 26 is slighted tapered. The annular wall 26 is sloped forming an angle 32 with a horizontal axis 30. In this embodiment the angle 32 is an obtuse angle, preferably about 95°, but may be a different angle, such as, for example, in the range of from about 85° to about 95°. In other embodiments, the angle 32 may be an acute angle or the stoma-receiving aperture 12 may be defined by a single annular wall (i.e. the angle 32 may be 90°). The oval aperture 12 has a major radius 22 along a major axis 21 and a minor radius 24 along a minor axis 23 (FIG. 2). The major radius 22 and the minor radius 23 are measured from the center 25 of the oval aperture to the lower annular wall 28. The major radius 22 is larger than the minor radius 24. In this embodiment, the major radius 22 is at least about 1.2 times the minor radius 24, preferably between about 1.4 and about 1.8 times the minor radius 24.

The convex top surface 18 of the barrier ring 10 includes a central portion 34 proximate the stoma-receiving aperture 12. The central portion 34 can have a generally flat surface having a cat-eye shaped perimeter 35 with a shape similar to the overall shape of the barrier ring body 11. The cat-eye shaped perimeter 35 terminates at tips 54, 56 at either end thereof, with end portions of the central portion 34 at 58, 60. The end portions 58, 60 of the central portion 34 terminate in tips. The central portion 34 is the thickest portion of the barrier ring 10 with a thickness 36 (FIGS. 6 and 7), and thus, defines the highest point of the barrier ring 10 that can apply the most pressure around the stoma (not shown.)

Figure 7:
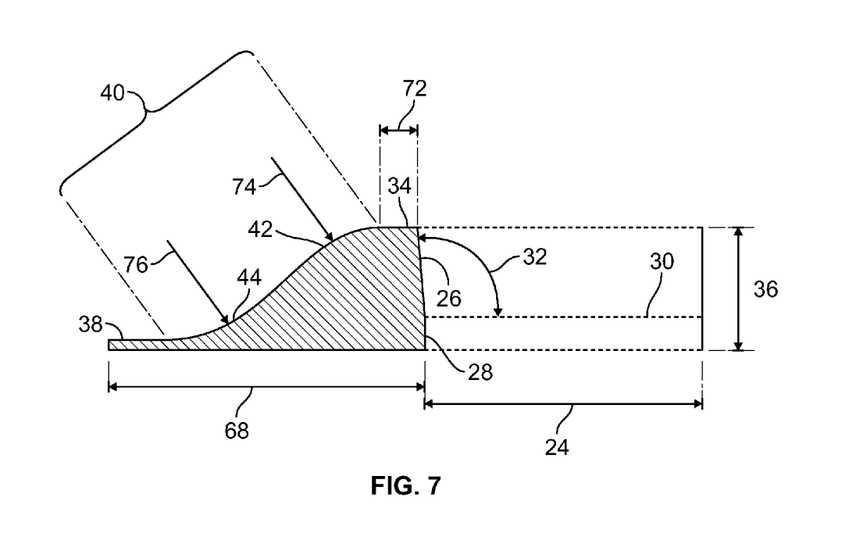
FIG. 7 is a partial cross-sectional view of the convex barrier ring of FIG. 1 taken along line A-A of FIG. 2.

A first half 46 of the barrier ring 10 above the major axis 21 and a second half 48 below the major axis 21 are preferably symmetrical about the major axis 21. The top surface 18 slopes down with a curved contour 40 from the central portion 34 to a peripheral portion 38, which also has a generally flat surface. The curved contour 40 includes a convex portion 42 and a concave portion 44 as shown in FIGS. 1 and 7. FIG. 7 show a partial cross-sectional view of the first half 46 of the barrier ring 10 along line A-A (FIG. 2). Since the barrier ring 10 is symmetrical about the major axis 21, a cross-sectional view of the bottom half 48 of the barrier ring 10 taken along the sectional line A-A will be the same as that shown in FIG. 2. Further, the convex top surface 18 of each of the first half 46 and the second half 48 of the barrier ring 10 has the same curved contour 40 including the convex portion 42 and the concave portion 44. The first half 46 and the second half 48 of the barrier ring 10 meet at the elongated tapered peripheral end portions 14, 16, wherein ridges 50, 52 are formed.

Figure 6:
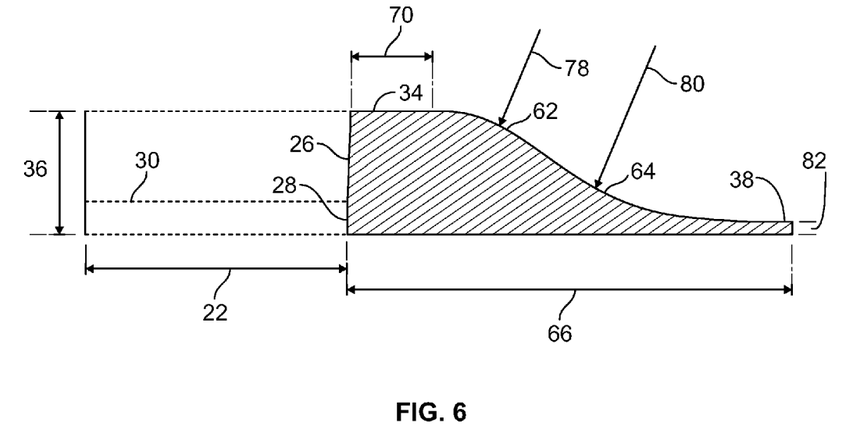
FIG. 6 is a partial cross-sectional view of the convex barrier ring of FIG. 1 taken along line B-B of FIG. 2.

As shown in FIGS. 1 and 2, the ridges 50, 52 extend down from tips 54, 56 of the cat-eye shaped center portion 34 to the peripheral portion 38 of the tapered peripheral end portions 14, 16. FIG. 6 shows a partial cross-sectional view of the tapered peripheral end portion 16 taken along the ridge 52 at line B-B. As shown in FIG. 6, the ridges 50, 52 have a convex portion 62, and a concave portion 64. The barrier ring 10 is also symmetric about the minor axis 21, thus, a cross-sectional view of the tapered peripheral end portion 14 along the ridge 50 will be same as the cross-sectional view of the tapered peripheral end portion 16 shown in FIG. 6.

The convex barrier 10 can be made in various sizes to fit various stoma sizes and peristomal skin surfaces. In one embodiment, the convex barrier ring 10 has the oval stoma-receiving aperture 12 with a major radius 22 of between about 0.5 inches and about 1.5 inches, preferably between about 0.7 inches and about 1.2 inches. The convex barrier ring 10 has a width 66 at the elongated tapered peripheral end portions 16 as seen along line B-B (FIG. 6) of between about 0.5 inches and about 1.5 inches, preferably between about 0.8 inches and about 1.1 inches; and a width 68 as seen along line A-A (FIG. 7) of between about 0.3 inches and about 1.0 inches, and preferably between about 0.5 inches and about 0.8 inches. The center portion 34 of the convex barrier ring 10 has a width 70 at the elongated edge 60 as seen along line B-B (FIG. 6) of between about 0.15 inches and about 0.35 inches, preferably between about 0.20 inches and about 0.30 inches; and a width 72 as seen along line A-A (FIG. 7) of between about 0.03 inches and about 0.12 inches, preferably between about 0.05 inches and about 0.08 inches. The barrier ring 10 has the thickness 36 at the center portion 34 of between about 0.15 inches and about 0.5 inches, preferably between about 0.2 inches and about 0.3 inches.

Figure 8:
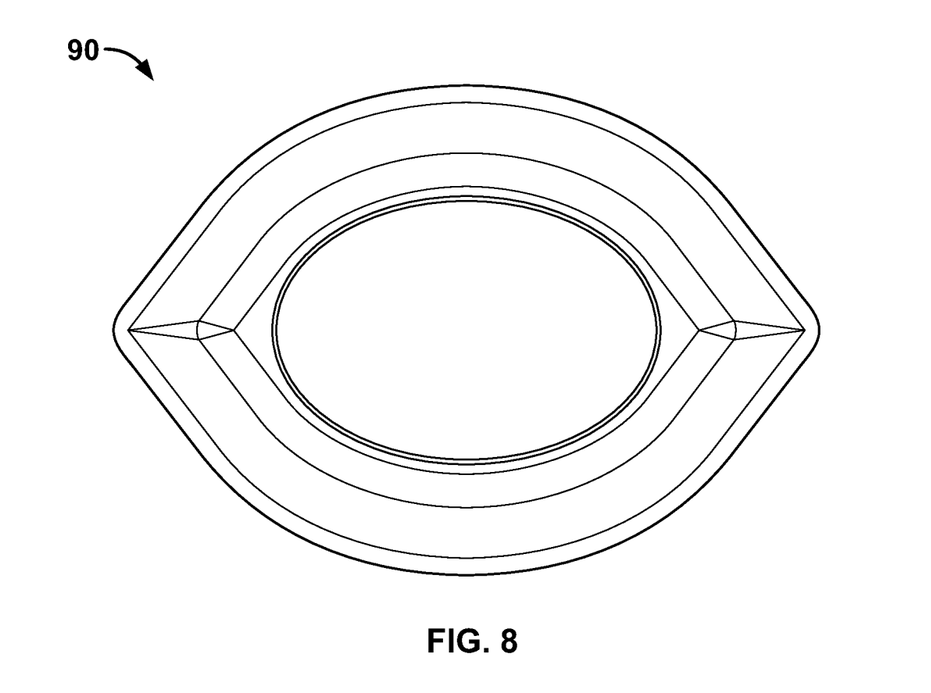
FIG. 8 is a top view of a convex barrier ring according to another embodiment.
Figure 9:
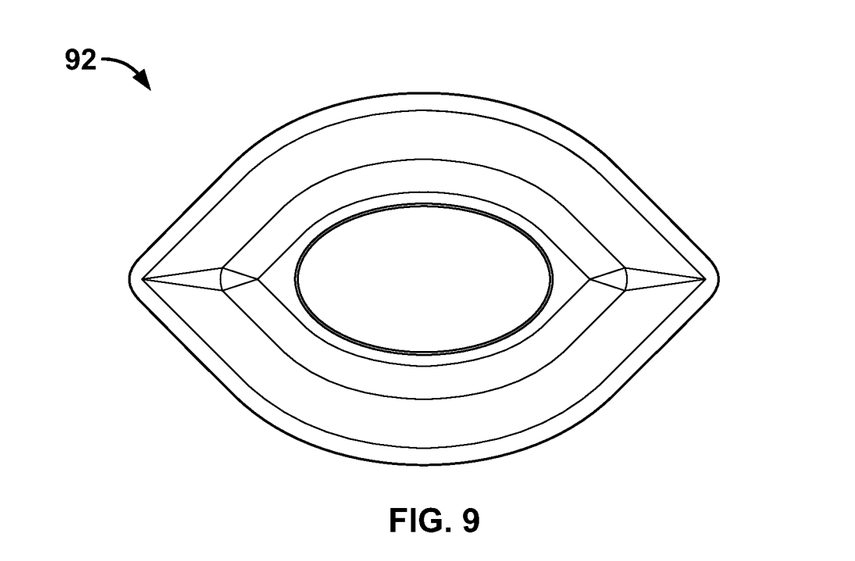
FIG. 9 is a top view of a convex barrier ring according to yet another embodiment.

Further, in the illustrated embodiment, the convex portion 42 of the curved contour 40 along line A-A (FIG. 7) has a radius 74 between about 0.15 inches and about 0.35 inches, preferably between about 0.20 inches and about 0.30 inches. The concave portion 44 has a radius 76 between about 0.30 inches and about 0.45 inches, preferably between about 0.35 inches and about 0.40 inches. The convex portion 62 of the ridge 52 along line B-B (FIG. 6) has a radius 78 between about 0.25 inches and about 0.40 inches, preferably between about 0.30 inches and about 0.35 inches. The concave portion 64 has a radius 80 between about 0.40 inches and about 1.10 inches, preferably between about 0.50 inches and about 0.75 inches. The flat peripheral portion 38 has a thickness 82 (FIG. 6) of between about 0.01 inches and about 0.04 inches, preferably between about 0.015 inches and about 0.025 inches. FIGS. 8 and 9 show a top view of convex barrier rings 90, 92 having different sizes and dimensions according to other embodiments.

EXAMPLES

Dimensional details of three preferred embodiments of the convex barrier ring 10 are provided below in Table 1.

TABLE 1

Convex Oval Barrier Ring Examples

| Dimensions (Reference numbers correspond to FIGS. 1-7) | Example 1 (inches) | Example 2 (inches) | Example 3 (inches) |
| --- | --- | --- | --- |
| Major radius 22 - oval stoma-receiving aperture | 0.945 | 0.748 | 1.102 |
| Minor radius 24 - oval stoma-receiving aperture | 0.591 | 0.433 | 0.748 |
| Barrier width 66 along major axis | 1.034 | 0.981 | 0.894 |
| Barrier width 68 along minor axis | 0.670 | 0.670 | 0.670 |
| Center portion width 70 along major axis | 0.272 | 0.219 | 0.230 |
| Center portion width 72 along minor axis | 0.068 | 0.068 | 0.068 |
| Radius 78 of convex portion 62 along major axis | 0.340 | 0.339 | 0.302 |
| Radius 80 of concave portion 64 along major axis | 0.724 | 0.724 | 0.578 |
| Radius 74 of convex portion 42 along minor axis | 0.250 | 0.250 | 0.250 |
| Radius 76 of concave portion 44 along minor axis | 0.375 | 0.375 | 0.375 |
| Thickness 82 of barrier at peripheral portion | 0.020 | 0.020 | 0.020 |
| Thickness 36 of barrier at center portion | 0.250 | 0.250 | 0.250 |

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A barrier ring adapted for attaching an ostomy appliance to a peristomal skin surrounding a stoma, the barrier ring comprising:
    a cat-eye shaped body defining a major axis and a minor axis and having elongated peripheral end portions that taper along the major axis of the cat-eye shaped body;
    a convex proximal bodyside surface;
    a flat bottom surface; and
    a stoma-receiving apertures;
    wherein the elongated peripheral end portions include ridges that are configured to fit in skin folds or creases to improve a seal between the barrier ring and the peristomal skin.

2. The barrier ring of claim 1, wherein the convex proximal bodyside surface includes a center portion proximate the stoma-receiving aperture, a peripheral portion, and a surface extending down from the center portion to the peripheral portion with a curved contour.

3. The barrier ring of claim 2, wherein each of the center portion and the proximal portion has a flat surface; wherein a thickness of the barrier ring at the center portion is larger than a thickness at the peripheral portion.

4. The barrier ring of claim 1, wherein the barrier ring is symmetrical about the major axis and the minor axis.

5. The barrier ring of claim 1, wherein the stoma-receiving aperture defines an oval shaped periphery, wherein a major radius of the stoma-receiving aperture is greater than about 1.2 times a minor radius.

6. The barrier ring of claim 1, wherein the barrier ring is formed of a pressure sensitive adhesive composition.

7. A convex barrier ring adapted for attaching an ostomy appliance to a peristomal skin surrounding a stoma, the convex barrier ring comprising:
    a convex proximal bodyside surface;
    a flat bottom surface;
    an oval stoma-receiving aperture; and
    a cat-eye shaped body defining a major axis and a minor axis and having elongated peripheral end portions that taper along the major axis of the cat-eye shaped body, wherein each of the elongated peripheral end portions includes a ridge extending down from proximate the stoma-receiving aperture to the elongated peripheral end portions, wherein the ridges are configured to fit in skin folds or creases to improve a seal between the convex barrier ring and the peristomal skin.

8. The convex barrier ring of claim 7, wherein the oval stoma-receiving aperture has a major radius and a minor radius, and wherein the major radius is between about 1.4 and about 1.8 times the minor radius.

9. The convex barrier ring of claim 7, wherein the convex proximal bodyside surface includes a center portion proximate the oval stoma-receiving aperture, a peripheral portion, and a surface extending down from the center portion to the peripheral portion with a curved contour.

10. The convex barrier ring of claim 9, wherein the curved contour includes a convex portion and a concave portion.

11. The convex barrier ring of claim 9, wherein the center portion has a cat-eye shaped periphery having elongated peripheral end portions, wherein each of the ridges extends down from a tip of each of the elongated peripheral end portions of the center portion to the peripheral portion.

12. The convex barrier ring of claim 7, wherein a contour of the convex proximal bodyside surface is symmetrical about the major axis and about the minor axis.

13. The convex barrier ring of claim 7, wherein the convex barrier ring is formed of a skin barrier material.

14. The convex barrier ring of claim 13, wherein the skin barrier material is a pressure sensitive adhesive composition.

15. A barrier ring adapted for attaching an ostomy appliance to a peristomal skin surrounding a stoma, comprising:
    a cat-eye shaped body defining a major axis and a minor axis and having elongated peripheral end portions that taper alone the major axis of the cat-eye shaped body;
    a bodyside surface;
    a bottom surface;
    a stoma-receiving aperture; and
    wherein the bodyside surface, when viewed in a cross-section taken along the major axis defines a convex surface transitioning to a concave surface from the stoma-receiving aperture to a respective elongated peripheral end portion, wherein the elongated peripheral end portions include ridges that are configured to fit in skin folds or creases to improve a seal between the barrier ring and the peristomal skin.

16. The barrier ring of claim 15, wherein a cross-section taken along the minor axis defines a convex surface transitioning to a concave surface from the stoma-receiving aperture to a respective peripheral portion of the barrier ring.

17. A method adapted for of attaching an ostomy appliance to peristomal folded or creased skin surfaces surrounding a stoma of a wearer, the method comprising:
    providing a convex barrier ring comprising:
        a convex proximal bodyside surface;
        a flat bottom surface;
        an oval stoma-receiving aperture; and
        a cat-eye shaped body defining a major axis and a minor axis and having elongated peripheral end portions that taper along the major axis of the cat-eye shaped body, wherein the elongated peripheral end portions include ridges that are configured to fit in skin folds or creases to improve a seal between the convex barrier ring and the peristomal folded or creased skin surfaces;
    placing the flat bottom surface on an adhesive side of a faceplate of the ostomy appliance;
    arranging the ostomy appliance assembled with the convex barrier ring around the stoma such that the stoma is arranged in the oval stoma-receiving aperture;
    sealing the convex proximal bodyside surface against the peristomal folded or creased skin surfaces such that the elongated peripheral end portions are aligned with the skin folds or creases.

18. The method of claim 17, wherein sealing the convex proximal bodyside surface includes aligning the elongated peripheral end portions such that the ridges are arranged in the skin folds or creases to improve the seal between the convex barrier ring and the peristomal folded or creased skin surfaces and to reduce leakage.

* * * * *